(12) United States Patent
Tada et al.

(10) Patent No.: US 7,312,053 B2
(45) Date of Patent: Dec. 25, 2007

(54) METHOD AND SYSTEM FOR DETECTION OF NUCLEIC ACIDS

(75) Inventors: Sachiyo Tada, Kobe (JP); Tomokazu Yoshida, Kobe (JP); Keiichiro Shohmi, Kobe (JP); Masahiro Nishida, Kobe (JP); Kazuki Nakabayashi, Kobe (JP); Koichi Yamagata, Kobe (JP)

(73) Assignee: Sysmex Corporation, Kobe (JP)

( * ) Notice: Subject to any disclaimer, the term of this patent is extended or adjusted under 35 U.S.C. 154(b) by 405 days.

(21) Appl. No.: 10/491,981

(22) PCT Filed: Jan. 8, 2003

(86) PCT No.: PCT/JP03/00060

§ 371 (c)(1),
(2), (4) Date: Apr. 7, 2004

(87) PCT Pub. No.: WO03/060116

PCT Pub. Date: Jul. 24, 2003

(65) Prior Publication Data

US 2005/0089857 A1    Apr. 28, 2005

(30) Foreign Application Priority Data

Jan. 9, 2002 (JP) .............................. 2002-002046
Nov. 13, 2002 (JP) .............................. 2002-329958

(51) Int. Cl.
*C12P 19/34* (2006.01)
*C12Q 1/68* (2006.01)

(52) U.S. Cl. .......................................... 435/91.2; 435/6

(58) Field of Classification Search ...................... None
See application file for complete search history.

(56) References Cited

U.S. PATENT DOCUMENTS 5,620,869 A * 4/1997 Woodard et al. ........... 435/91.1
6,090,316 A   7/2000 Zhu et al.
6,455,692 B1 * 9/2002 Gjerde et al. ............... 536/25.4
7,005,266 B2 * 2/2006 Sprenger-Haussels .......... 435/6
7,101,663 B2 * 9/2006 Godfrey et al. ................ 435/6

FOREIGN PATENT DOCUMENTS

| EP | 0 854 195 | 8/1998 |
| EP | 1042497 A1 | 10/2000 |
| JP | 2002-50508 A | 2/2002 |
| WO | 98/44101 | 10/1998 |
| WO | WO99/32654 A1 | 7/1999 |
| WO | 01/57247 | 8/2001 |

OTHER PUBLICATIONS

Shin et al (J. Clinical Microbiology (1997) 35(6):1454-1459).*
Good et al (Biochemistry (1966) 5(2):467-477).*
Klebe RJ et al., RT-PCR with out RNS isolation, Biotechniques, Dec. 1996, vol. 21, No. 6, pp. 1094 to 1100.
Himanit et al, *Plant Physiology*, 123(4):1203-1212 (2000).

* cited by examiner

*Primary Examiner*—Kenneth R. Horlick
(74) *Attorney, Agent, or Firm*—Sughrue Mion, Pllc.

(57) ABSTRACT

In detecting a nucleic acid by using the nucleic acid amplification method, it is intended to shorten the time required for the measurement so as to systematically and efficiently examine a gene, etc. To achieve this object, use is made of a method of directly amplifying a nucleic acid by treating a collected biological sample wherein a means of inhibiting the degradation activity of the nucleic acid is introduced during or after the step of homogenizing the biological sample and thus the nucleic acid is directly amplified without isolating/purifying the nucleic acid component from the biological sample. In this method, the means of inhibiting the degradation activity of the nucleic acid is introduced at an acidic pH value (more specifically, from pH 2.5 to pH 5) with the use of a salt interacting with a substance inhibiting the nucleic acid amplification reaction and/or the nucleic acid component so as to directly amplify the nucleic acid without isolating/purifying the nucleic acid component.

15 Claims, 7 Drawing Sheets

① 200mM KCl-HCl(pH1.0)+0.1%NONIDET P-40
② 200mM KCl-HCl(pH2.2)+0.1%NONIDET P-40
③ 200mM KCl-HCl(pH3.0)+0.1%NONIDET P-40
④ 200mM Glycine-HCl(pH3.0)+0.1%NONIDET P-40
⑤ Acetic acid buffer(pH5.2)+0.1%NONIDET P-40
⑥ 50mM Tris-HCl(pH7.4)+0.1%NONIDET P-40
⑦ No Buffered solution (H$_2$O)

METHOD AND SYSTEM FOR DETECTION OF NUCLEIC ACIDS

This application claims priority from Japanese Patent Application No. 2002-002046 and No. 2002-329958 incorporated herein by reference.

FIELD OF THE INVENTION

The present invention relates to a method for treating biological samples containing nucleic acids, and more specifically, to the method which enables simply and quickly detecting genes of interest by a nucleic acid amplification, without directly extracting the nucleic acid components from biological sample, in a field where a diagnosis of tumors and cancers, a detection of the infection with viruses and bacteria, as well as various genetic diseases using means for the nucleic acid amplification are performed.

BACKGROUND OF THE INVENTION

Recent advances in gene technology and molecular biology have made diagnoses of diseases such as infectious diseases and genetic diseases possible at levels of DNA and RNA. Gene analysis has been immensely facilitated by the method for the nucleic acid amplification such as polymerase chain reaction (PCR; Science, 230: 1350-1354, 1985), NASBA (Nucleic Acid Sequence Based Amplifications, Nature, 350, 91-92,1991;

Japanese Patent No. 2648802; Japanese Patent No. 2650159) and LAMP (Loop mediated isothermal amplification of DNA, Japanese Patent Laid-open Publication No. 2001-242169) in particular, through which a detection of a trace amount of nucleic acids in biological samples, which had been extremely difficult to detect, has become possible.

PCR is a method which enables to amplify an objective DNA fragment hundreds of thousands-fold by repeating a cycle of a dissociation of double strands of DNA into single strands, binding of primers to sequences flanking specific region of DNA strands and a DNA synthesis by a DNA polymerase. The method was invented by Mullis and others, and is described in Japanese Patent Laid-open Publication No. S61-274697. PCR can be used as a sensitive method for analyzing nucleic acids from various samples and particularly useful for analyzing nucleic acids in samples derived from body fluids of animals. Accordingly, PCR is utilized for diagnoses of infectious diseases, genetic diseases and cancers. Moreover, the method is suitable for a typing of DNA upon a transplantation and an identification of a parent-child relationship. In these cases, peripheral blood is often used as a sample to be examined.

One of drawbacks of PCR is that the reaction is interfered by pigments, proteins, sugars and other unknown contaminants. In fact, it is widely known that in addition to the most frequently used a thermoresistant DNA polymerase, a TaqDNA polymerase derived from *Thermas aquaticus*, a number of DNA polymerases are strongly inhibited by the presence of a trace of contaminants derived from body fluids.

RT-PCR is a method where RNA extracted from, for instance, tumor tissues, is converted to cDNAs by a reverse transcriptase (RT), by using an origo (dT) or a random hexamer as a primer, part of cDNAs are utilized for a PCR amplification, then used for detection. A case using this method to diagnose a fibloblastoma is reported (Hokkaido Igaku Zasshi, p.135-141, Vol. 66(2), 1991). Since RT-PCR relies on mRNA which is prone to be degraded, a quick treatment is required after collection of a sample. Furthermore, special care has to be taken to prevent the sample from a contamination of others, as RT-PCR is an extremely sensitive method for detection of DNA.

LAMP is a method for a gene amplification by using more than two sets of primers comprising special primers that form hairpin structures at a distal ends of amplification products as strand displacement reaction proceeds. Amplification products consisted of many repeated structures, whose unit of repeating structure consists of a complementary region in the same strands wherein base sequences of a double-stranded nucleic acid are reversed. Although amplification products of LAMP can be detected by a publicly known method for detection of double-stranded DNA, a detection method taking advantage of their unique structure is reported (Japanese Patent Laid-open Publication No. 2001-242169, WO 00/28082).

Other lines of the method for the gene amplification, TMA, NASBA, and 3SR, are characterized in the use of primers carrying the T7 promoter sequence in one of two primer strands. Therefore, when these primers are hybridized to a target DNA or RNA followed by a reverse transcription (a DNA synthesis using RNA or DNA as a template), a double-stranded DNA with a T7 promoter is synthesized. A large amount of RNA are synthesized as the amplified product by addition of a T7 polymerase to this reaction system, as a result of the activation of the T7 promoter followed by expression of downstream genes. In TMA, NASBA and 3SR, amplification cycles described above proceed at a constant temperature.

A system for detection of nucleic acid utilizing means for nucleic acid amplification is generally composed of a process for treatment of biological materials, a process of extracting of nucleic acids, a process for dispensing measuring reagents, a process for the nucleic acid amplification and a process for an assessment of amplification products. A process of preliminary treatment for the extraction of nucleic acids is needed prior to the nucleic acid amplification by methods such as a PCR method. The methods for nucleic acids extraction have been used wherein gene-containing materials are degraded by an enzyme,a surfactant or a chaotropic agent, then a treatment by phenol (Biochemica et Biophysica Acta, 72: 619-629,1963), alkaline conditions (Nucleic Acid Research, 7: 1513-1523,1979), or phenol-chloroform and so on are carried out. Recently, ion-exchange resins, a glass filter, glass beads or a reagent having an aggregating activity for proteins are used in the process of nucleic acids extraction.

As a system utilizing a nucleic acid-binding carrier for an extraction of nucleic acids, a method of using glass particles and sodium iodide (Proc.Natl.Acad.Sci.USA, 76-2: 615-619, 1979) and a method using hydroxyapatite (Japanese Patent Laid-open Publication No; S63-263093) and so on are reported. In these methods, whereas a use of toxic reagents such as an organic solvent is limited, instead there is a problem in that it takes long time to isolate nucleic acids due to repeated centrifugation during the process, making it difficult to handle many samples at a time.

As described, conventional methods for an isolation of nucleic acids have disadvantages in that they employ dangerous reagents such as the organic solvent and alkaline substances, they require centrifugation steps, making it difficult to handle many samples at a time. The disadvantage becomes even more serious in view of automation, in which many samples are treated with high reproducibility to reduce personal costs.

As a method for automating the process for the extraction of nucleic acids, there is a method of using nucleic acid-binding silicate particles and chaotropic ions (J. Clinical Microbiology, 28-3: p.495-503, 1990, Japanese Patent Publication No. 2680462). In this method, by mixing nucleic acid-binding silicate particles and chaotropic ion having an ability to isolate nucleic acids in the sample and the sample, nucleic acids are first combined with nucleic acid-binding silicate particles, allowing a separation of a solid phase from a liquid phase to remove contaminants in the sample, followed by an elution of nucleic acids bound to nucleic-acid binding silicate particles.

Acid treatment of biological samples comprising nucleic acids is reported (International Publication WO 01/00813) as means for removing inhibitory substances on the nucleic acid amplification. However, in spite of the description on the possibility of acid treating biological samples at any given stage for the extraction of nucleic acids from the biological samples, it remains difficult to carry out rapid nucleic acid amplification since no description has been given with regard to conducting the nucleic acid amplification without isolation and the purification of nucleic acids.

A method is reported wherein samples are brought into contact with an anionic solid phase to facilitate the binding of inhibitory substances on the nucleic acid amplification, as means for reducing the inhibition on reaction of nucleic acid amplification (Japanese Patent Laid-open Publication No. 1997-173065). However, it is still difficult to conduct a rapid nucleic acid amplification, since no description was given herein, with regard to carrying out the nucleic acid amplification without isolation and purification of nucleic acids.

The above-mentioned methods for the nucleic acid amplification have been put to practical use in the field of diagnoses of tumors and cancers, a detection of virals as well as bacterial infections, and a detection of various genetic diseases (Handbook of the method of clinical examination, $_{31}$st edition, Kanahara & Co., Ltd, published on Sep. $20^{th}$, 1998).

However, many aspects are left to be improved in terms of a necessary time for a measurement and sensitivity in the detection of nucleic acids by way of the nucleic acid amplification.

DISCLOSURE OF THE INVENTION

An object of the present invention is to make an examination system for genes and the like efficient as a whole by shortening the necessary time for the measurement in detecting nucleic acids by using the method for the nucleic acid amplification.

As a result of intensive studies on solving the problem by the present inventors, the present invention was completed by finding that a necessary time for the examination system as a whole could be shortened and sensitivity of the measurement could be heightened when the process for preliminary treatment of biological samples was improved.

Accordingly, the invention includes:
1. A method for a direct nucleic acid amplification, comprising introduction of means for inhibiting degradation activity of the nucleic acid to amplify the nucleic acid without isolating and purifying a nucleic acid component from a biological sample;
2. The method for a nucleic acid amplification according to Item 1, wherein the means for inhibiting the degradation activity of the nucleic acid-is means for inhibiting the RNA degradation activity;
3. The method for a nucleic acid amplification according to Item 1 or 2, wherein the introduction of the means for inhibiting the activity of degradation is carried out at an acidic pH;
4. The method for a nucleic acid amplification according to Item 3, wherein the acidic pH is pH2.5-pH5;
5. The method for a nucleic acid amplification according to any of Items 1 to 4, wherein the amplification of the nucleic acid is carried out without isolating and purifying the nucleic acid after a process of homogenization of the collected biological sample;
6. A method for a nucleic acid amplification a nucleic acid, comprising treatment of a biological sample with a salt which interacts with an inhibitor of an amplification reaction and/or a nucleic acid component to amplify the nucleic acid without isolating and purifying the nucleic acid component;
7. The method for a nucleic acid amplification according to Item 6, wherein the interaction of the salt with the inhibitor is carried out according to ionic bond and/or hydrophobic bond;
8. The method for a nucleic acid amplification according to Item 6 or 7, wherein the salt is a chaotropic salt;
9. The method for a nucleic acid amplification according to Item 6 or 7, wherein the salt is an alkaline metal salt of trihaloacetic acid;
10. The method for a nucleic acid amplification according to Item 8, wherein the salt is at least one selected from NaCl, KCl, NaI, KI, TMAC1 (tetramethyl ammonium chloride), TEAC1 (tetraethyl ammonium chloride), KSCN, CsSCN and CsCl;
11. The method for a nucleic acid amplification according to Item 9, wherein the salt is $CF_3COOCs$ (cecium trifluoroacetate);
12. The method for a nucleic acid amplification according to any of Items 6 to 11, wherein concentration of the salt is 1 mM-2000 mM;
13. The method for a nucleic acid amplification according to any of Items 6 to 12, wherein a biological sample is treated by introducing means for inhibiting degradatin activity of nucleic acid and further using a salt interacting with an inhibitor of the amplification reaction;
14. The method for a nucleic acid amplification according to Item 13, wherein means for inhibiting activity to degrade the nucleic acid is means for inhibiting the RNA degradation activity;
15. The method for a nucleic acid amplification according to any of Items 12 to 14, wherein the introduction of means for inhibiting the degradation activity is carried out at an acidic pH;
16. The method for a nucleic acid amplification according to Item 15, wherein the acidic pH is pH2.5-pH5;
17. The method for a nucleic acid amplification according to any of Items 6 to 16, wherein the amplification of the nucleic acid is carried out without isolating and purifying the nucleic acid after a process of homogenization of the collected biological sample;
18. The method for a nucleic acid amplification according to any of Items 6 to 17, wherein the biological sample is further treated with an anionic solid material after the treatment with the salt which interacts with the reaction inhibitor and/or the nucleic acid component;
19. The method for a nucleic acid amplification according to any of Items 6 to 18, wherein the amplification of the biological sample treated with the salt which interacts with the reaction inhibitor and/or nucleic acid component is carried out in the presence of a nuclease inhibitor;

20. The method for a nucleic acid amplification according to Item 19, wherein the nuclease inhibitor is a RNase inhibitor;
21. The method for a nucleic acid amplification according to any of Items 1 to 20, wherein the method of the amplification of a nucleic acid is selected from LAMP, RT-LAMP, PCR and RT-PCR;
22. A method for treating a biological sample used for the method of the amplification of a nucleic acid according to any of Items 1 to 20;
23. A reagent for detection of a nucleic acid used for the method of the amplification of a nucleic acid according to any of Items 1 to 20;
24. A system for detection of a nucleic acid, the system utilizing the method of the amplification of a nucleic acid according to any of Items 1 to 20;
25. An apparatus for a nucleic acid test, the apparatus employing the system for detection of a nucleic acid according to Item 24;
26. A method for cancer metastasis test, the method employing the system for detection of a nucleic acid according to Item 24;
27. A kit for a nucleic acid test, the kit being used for the system for detection of a nucleic acid according to Item 24;
28. A solution for treatment of a biological sample, the solution having pH to maintain a nucleic acid component a stable state;
29. The solution for treatment of a biological sample according to Item 28, wherein the pH is 2.5-5; and
30. The solution for treatment of a biological sample according to Items 28 or 29, further comprising a salt interacting with an inhibitor of the nucleic acid amplification reaction and/or a nucleic acid component.

BEST MODE FOR CARRYING OUT THE INVENTION

Figure 1:
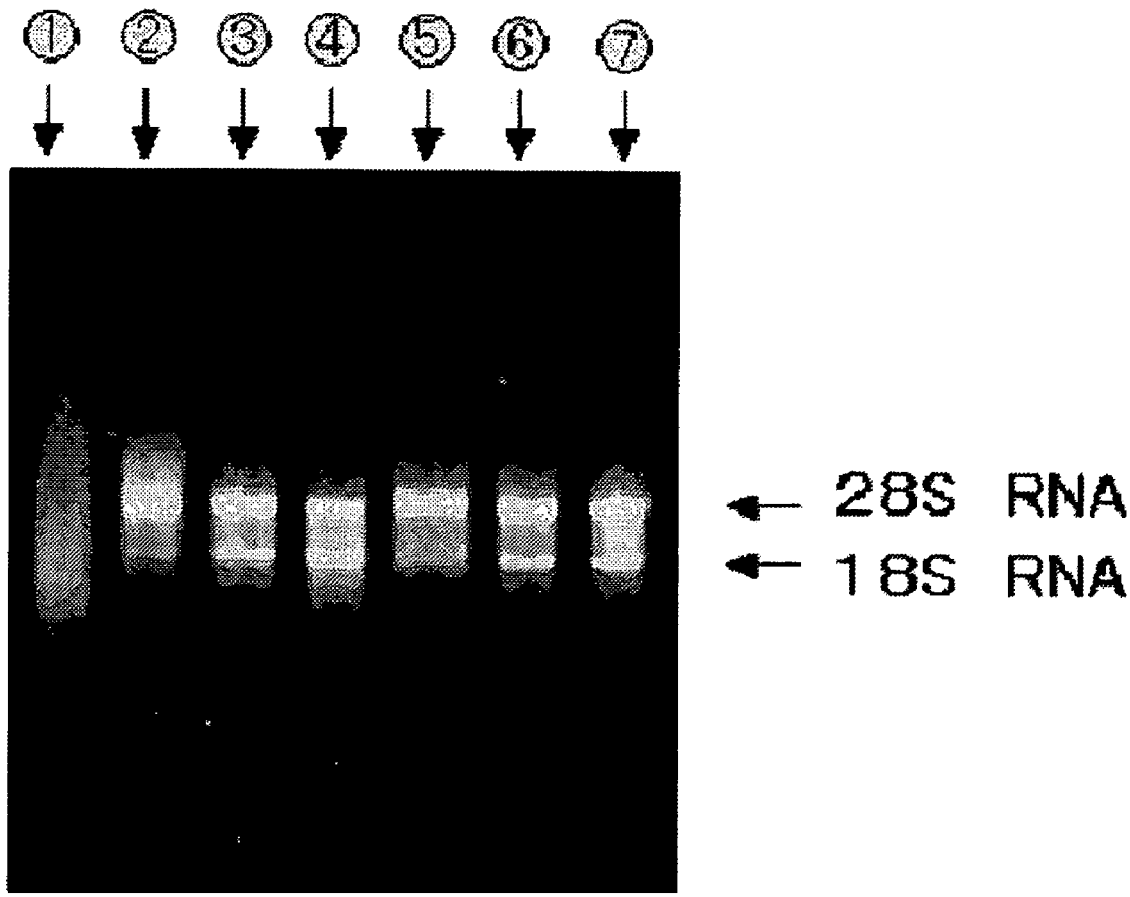
FIG. 1 shows a stability of extracted RNA (Example 1).

The method for the nucleic acid amplification, the method of the treatment of biological samples, reagents used for the detection of nucleic acids according to the present invention are described below.
A method for a direct nucleic acid amplification according to the present invention means a method for the nucleic acid amplification that enables an amplification of the nucleic acid contained in the biological sample obtained from an organism to be examined after homogenization of the biological sample by a blender and the like and, more specifically, and means a method that enables a direct nucleic acid amplification of the without an extraction of an objective nucleic acid component from a homogenized biological sample.

The biological sample in the present invention means a sample obtainable from a living organism for the amplification of the objective nucleic acid. Specifically, it includes biological samples originated from human or animal such as tissues, whole blood, serum, plasma, urine, saliva, body fluid and secreted materials collected from the living body and in addition, biological materials other than animals such as plants and microorganisms.

(Treatment of Biological Samples)

Introduction of means for inhibiting the nucleic acid degradation activity means to introduce substances or conditions that inhibit the activity of substance responsible for degradation of nucleic acids, for example nucleases, contained in a biological sample upon treatment of the biological sample. Here, nucleic acids mean DNA or RNA and, for example, RNA, particularly mRNA is preferably applied for confirming an expression of protein. RNA is prone to be degraded by RNase contained in a living organism component and is particularly unstable. Means for inhibiting a nucleic acid degradation activity in the present invention is, specifically for instance, means for inhibiting an activity of DNase or RNase. In this case, means such as an addition a nuclease inhibitor is generally considered. In addition, any means can be chosen as long as means are capable of inhibiting the activity of degrading nucleic acids in the present invention. For example, as means for inhibiting the nuclease activity, means for inhibiting the enzyme activity can be applied by a degeneration of enzyme proteins. Means for degeneration of enzyme proteins includes an addition of a protein denaturing agent, a heat treatment, and a degenerating treatment by changing pH. In the present invention, it is required to degenerate enzyme proteins and maintain objective nucleic acid components at stable state.

As a result of examining the condition for remaining the objective nucleic acid component stable, it became clear that the stability of the nucleic acid contained in the biological sample varies depending on pH of a solution for treating the biological sample. Neutral pH of a treatment solution, where an enzyme activity of nuclease is the highest, is not preferable. At the more acidic conditions (at lower pH), nucleic acid components, particularly RNA is degraded to short fragments by chemically degradation of phosphodiester bond. Thus pH 2 or lower is not preferable too. One of characteristics of the present invention is that biological specimens are treated under neutral or lower pH and it is found the condition where objective nucleic acids can be remained stable. Practically, objective nucleic acid components can be remained stable by treating the biological sample with a solution having pH2.5-5, preferably pH3-4, and more preferably around pH3.

Solutions having an acidic pH include, practically, a solution containing glycine-HCl or potassium chloride-HCl.

The treatment of the biological sample described above can also be carried out by the addition of a salt that interacts with inhibitors of the nucleic acid amplification reaction. Inhibition of the nucleic acid amplification reaction, in the case of amplifying DNA using mRNA as a template for example, includes a repression of reverse transcription activity from mRNA, and a repression of DNA replication. A repression of the amplification may occur, for example, through binding of objective nucleic acids such as DNA or RNA to proteins in the sample.

When the biological sample is treated at the acidic pH, nucleic acid components such as RNA remain charged (−), whereas proteins tend to charge (+). Thus the nucleic acid component and protein bind through ionic bond or hydrophobic bond. In order to prevent the binding of the nucleic acid component with protein, a substance which interacts with proteins through ionic bond or hydrophobic bond can be added to treatment solution before the binding takes place. Such substance may be named as a salt interacting with an inhibitor of the reaction and/or nucleic acid components.

As practical examples of the salt which interacts with inhibitors of the nucleic acid amplification reaction and/or nucleic acid components, salts capable of generating a chaotropic ion, so called a chaotropic salt, and alkali metal salts of trihaloacetic acid can be mentioned. The chaotropic ion is a generic term for anionic monovalent ions with a large ionic radius. The ion has a function, when being added into water, to increase aqueous solubility of a hydrophobic molecule to weaken hydrophobic bond thereof. In fact, the nucleic acid amplification can be efficient by the weakness of the ability of the binding of the objective nucleic acid with the reaction inhibitor through ionic bond or hydrophobic bond by these ions to prevent adsorption of the objective nucleic acid to the reaction inhibitor. Examples of the chaotropic ion include $SCN^-$, $I^-$, $ClO_4^-$, $NO_3^-$, $Br^-$, $Cl^-$, $CH_3CO_2^-$ and $F^-$. Salts capable of generating these ions include NaCl, KCl, LiCl, RbCl, NaI, KI, TMACl, TEACl, KSCN, CsSCN and CsCl. Preferable salts are NaCl, KCl, NaI, KI, TMACl, TEACl, KSCN, CsSCN and CsCl. The above salt may be added before or after the introduction of the above mentioned means for inhibiting the activity to degrade nucleic acids, or at the same time. Simultaneous addition is most preferable from the viewpoint of efficiency.

Alkaline metal salts of trihaloacetic acid also can render the reaction of nucleic acid amplification efficient through the effect similar to that of chaotropic salts. Examples of alkaline metal salts of trihaloacetic acid include sodium trifluoroacetate, potassium trifluoroacetate, cesium trifluoroacetate, lithium trifluoroacetate, sodium trichloroacetate, potassium trichloroacetate, cesium trichloroacetate, lithium trichloroacetate, rubidium trichloroacetate and francium trichloroacetate. Preferable example is cesium trifluoroacetate. Above salts may be added before or after an introduction of the above mentioned means for inhibiting the activity to degrade nucleic acids, or at the same time. Simultaneous addition is most preferable from the viewpoint of efficiency.

Concentration of the additive salt is 1 mM-2000 mM, preferably 50 mM-500 mM, and more preferably 100 mM-300 mM.

Above biological samples, treated with the salt which interacts with a reaction inhibitor of the nucleic acid amplification reaction, may be treated with an anionic solid material, that is, a negatively charged solid material. As the anionic solid material, a cation exchange resin such as carboxymethyl-, phosphor- or sulfopropyl-derivatized ion exchange matrix or any other solid materials with negatively charged surface such as a negatively charged silica material may be used. Known methods may be utilized as a method for treatment of a biological sample with an anionic solid material such as a cationic exchange resin. Practically, a column chromatography and a batch method can be employed. For instance, a sample and anionic particles are mixed, and then anionic particles can be separated from objective nucleic acids together with the above described reaction inhibitor by means of centrifugation, standing, magnetic separation or such like.

In order to improve an effect of stability, publicly known surfactants may be used together. Examples of the surfactant include non-ionic surfactants, cationic surfactants, anionic surfactants and amphoteric surfactants. Preferably, the non-ionic surfactant is used. Examples of the non-ionic surfactant include higher alcohols, alkylphenols, ethyleneglycol or polyalcohol partial esters of fatty acid and the like, higher fatty acid glycerol esters, sorbitol fatty acid esters and addition polymerization products having polypropylene glycol as a hydrophobic group and ethylene glycol as a hydrophilic group at both ends thereof. These surfactants may be used independently or by mixing two or more of them.

To prepare a sample for measurement, the biological sample may be treated, after being disrupted and homogenized by using a homogenizer and/or the blender and the like, with the above mentioned means for inhibiting the nucleic acids degradation activity and/or the salt interacting with the reaction inhibitor of the nucleic acid amplification, and/or the anionic solid. The sample for measurement thus obtained can be used directly for the measuring method according to the present invention, this is major characteristics of the present invention that represents the method for the direct nucleic acid amplification. The homogenized biological sample may be subjected to treatment of filtration, centrifugation or the like in order to remove cell debris, if necessary.

(Process of Nucleic Acid Amplification)

The method for the nucleic acid amplification according to the present invention can be applied to those publicly known without particular limitation. It can be applied, for example, to a method for the nucleic acid-amplification such as PCR, RT-PCR, LAMP, RT-LAMP, TMA (Transcription Mediated Amplification) (Japanese Patent Laid-open Publication No. H4-500759), NASBA, 3SR, SDA (Strand Displacement Amplification), or ICAN (Isothermal and Chimeric primer-initiated amplification of Nucleic acids) and a signal amplification method that is one of kinds of the method for the nucleic acid amplification, such as RCA (Rolling Circle Amplification), INVADER, CPT (Cycling Probe Technology), or PALSAR. It is applied preferably to PCR, RT-PCR, LAMP and RT-LAMP, and more preferably to RT-PCR and RT-LAMP, wherein RNA is amplified, with particular effectiveness.

(Detection of Product of Amplification)

Usually, the product of the amplification after the completion of the reaction can be detected with publicly known methods without particular limitation. The method can be selected from, for example, an agarose gel electrophoresis, real time detection methods with probes utilizing a fluorescent label, a method based on detection of turbidity generated by a by-product of DNA synthesis, confirmation of fragments pattern digested with restriction enzymes or a method of determination of the base sequences by a direct sequence analysis, and many other methods if necessary. Furthermore, if it is difficult to identify specific bands because of the occurrence of the excess of non-specific amplified bands, the specific bands can be confirmed by a Southern blot method and the like, by using a probe within an objective amplified region. In the present invention, these known methods may be applied.

(Objective Nucleic Acids)

Though objective nucleic acids to which apply the above method may not be particularly limited, it maybe widely applied in a field of a clinical test where the presence or absence of disease is judged by amplifying minute amount of nucleic acids. For example, application is made to confirm an expression of cancer or tumor associated markers, genetic diseases, a judgment of the presence or absence of the infection by viruses or bacteria, and the like.

Among cancer or tumor associated markers, there are markers whose expression is equally positive in cancerous tissue of a cancer patient and normal position of the cancer-ridden organ while negative in the tissue to be diagnosed unless metastasis of the cancer took place, or the markers strongly expressed in cancer tissue, and the like.

Examples of markers whose expression is equally positive in cancerous tissues of the cancer patient and normal position of the cancer-ridden organ include cytokeratins, specifically, cytokeratin 18, cytokeratin 19, cytokeratin 20, and the like. An example of the marker strongly expressed in cancerous tissues, on the other hand, is a tumor marker such as CEA. Metastasis of cancerous cells can be detected by confirming mRNA for protein in objective tissues for diagnosis.

To confirm the above described mRNA derived from cancerous tissues observed in a specified patient, the amount of mRNA for proteins which are equally expressed in cancerous tissues as well as normal portion and objective tissues of the cancer-ridden organ, may be used as an index. Such examples are mRNA of β-actin and GAPDH.

Prompt diagnoses of cancer metastasis to lymph node, intraabdominal metastasis and the like are made possible by applying the method of the present invention. For example, in the case of breast cancer, it is preferable to keep a region of lymph node dissection as small as possible upon surgery, in consideration of an improvement of QOL (quality of life). In the case of esophageal cancer, selection is required, depending on the region of metastasis to lymph node, as to whether laparotomy, thoracotomy, or incision in the neck. For prostate cancer, decision as to whether surgery has to be continued or not is made in such a way that surgical excision of the cancer is replaced by hormonal therapy in case metastasis to lymph node is found. In the case of gastric cancer, region of dissection as well as the method of operation would vary greatly, depending on the presence or absence of the cancer metastasis to lymph node, which would give a suggestion on the post-operative treatment policy such as the choice of anticancer agent administration or radiation therapy. In these cases, if rapid diagnosis of cancer metastasis is made by using living tissues obtained in surgery, a patient will be able to receive the best treatment since it becomes possible to perform decision on the region of lymph node dissection, alteration in the method of operation, choice of adjunctive therapy and the like, during a short course of operation. The testing system of the present invention can be applied as a method for rapid diagnosis of the cancer metastasis during an operation.

In the case of gene-related disease, the present invention can be applied as a method for genetic disease test such as prognosis of the onset risk of genetic diseases which occur with aging, specifically, glaucoma, familial colon cancer, hypertension, diabetes and the like. In judging the presence or absence of viral and bacterial infection, it can also be applied to a rapid test for the presence or absence of the nucleotide sequence of substance responsible for infection in living tissue, for example, blood.

(Reagent, Testing Kit and Testing System)

The present invention can provide reagents of various kinds necessary for the method for the direct nucleic acid amplification, specifically, solutions for treating a biological sample, reverse transcriptase, DNTP used as a substrate for synthesizing complementary strands, DNA polymerase catalyzing the synthesis of the complementary strands in a strand displacement, oligo-nucleotides of various kinds needed as primers used in the present invention, buffers suitable for conditions to enzyme reaction, and various kinds of reagents needed for detecting reaction products if necessary.

Moreover, a kit can be provided by combining, among these reagents, a solution for treating a biological sample with at least one of the other reagents.

A scope of the present invention covers, in addition to the method of the direct nucleic acid amplification, methods for treating biological samples, reagents for detecting the nucleic acid including the method of treatment, kits and the whole system for the detection of the nucleic acid. Instruments and the method for the test of cancer to which the present system is applied are also covered. Specifically, the present system is applicable to the tissue from living body of a patient during operation, enabling detection of metastasis of cancer to the other tissues.

EXAMPLES

The present invention is described in more detail by examples below. However, the scope of the present invention is not restricted to these examples. Unless otherwise specified parts and percents are by weight.

Example 1

Conditions for remaining RNA-stable were examined.

1) Materials and Methods (1) Preparation of Sample

Lymph node was obtained from mouse and the tissue was disrupted by a homogenizer and a blender. The homogenate was centrifuged (12000 rpm×5 min) at 4° C. and the supernatant was collected. RNA was extracted from the supernatant by a commercially available reagent for extraction (TRIZOL: Gibco BRL made).

An aqueous solution of RNA 513 µg/ml obtained by extraction was examined for its stability in various buffers listed below. 2 µL of the above mouse RNA solution was added to 7 µL of each buffer and incubated for 10 min at room temperature. Then, stability of RNA was examined by agarose gel electrophoresis after the addition of 1 µL of an electrophoresis buffer.

(2) Buffers

① 200 mM of potassium chloride-HCl (pH 1.0)+0.1% of Nonidet P-40 (non-ionic surfactant: Calbiochem made)
② 200 mM of potassium chloride-HCl (pH 2.2)+0.1% of Nonidet P-40
③ 200 mM of potassium chloride-HCl (pH 3.0)+0.1% of Nonidet P-40
④ 200 mM of glycine-HCl (pH 3.0)+0.1% of Nonidet P-40
⑤ Acetate buffer (pH 5.2)+0.1% of Nonidet P-40
⑥ 50 mM of Tris-HCl (pH 7.4)+0.1% of Nonidet P-40
⑦ No buffer added (H₂O)

(3) Detection of RNA (Agarose Electrophoresis)

Agarose gel electrophoresis was carried out by commonly used method in 1% agarose, TEA buffer, by loading 1 µg/lane of RNA.

2) Results

The result is shown in FIG. 1. RNA was not digested in buffers higher than pH 3.0 and was shown stable. In buffers more acidic than pH 2.2, RNA was degraded and the bands for RNA were not recognized.

The buffer having pH 3.0 stabilized RNA, thus found to be the most effective as a buffer used for preparing RNA sample.

Example 2

Lymph node was obtained from a patient with breast cancer and the presence or absence of mRNA for cytokeratin (CK18 and CK19) was examined on human crude RNA sample and purified RNA samples by RT-PCR.

1) Materials and Methods (1) Preparation of Sample

Human lymph node was disrupted by a homogenizer and a blender in a buffer containing 50 mM of potassium chloride-HCl (pH 3.0)+0.1% of Nonidet P-40. The homogenenate was centrifuged (12000 rpm) at 4° C. and the supernatant was collected and used as a crude RNA sample. Then, a purified RNA sample was also prepared by extracting from an aliquot of the crude RNA sample with the commercially available reagent for extraction (TRIZOL: Gibco BRL made) as described in Example 1.

(1) Sequences of Primers and Probes Used (a) CK 18 reverse primer:

```
5'-GATGGTTTGCATGGAGTTGCT-3'    (sequence No. 1)
```

(position of the bases of CK18 sequence based on Genebank accession No. 4557887: 1215-1195)

(b) CK 18 forward primer:

```
5'-GCCGCCTGCTGGAAGAT-3'    (sequence No. 2)
```

(position of the bases of CK18 sequence based on Genebank accession No. 4557887: 1142-1158)

(c) CK 19 reverse primer:

```
5'-TCCAGGGCGCGCAC-3'    (sequence No. 3)
```

(position of the bases of CK19 sequence based on Genebank accession No. 4504916: 305-292)

(d) CK 19 forward primer:

```
5'-AAGCTAACCATGCAGAACCTCAAC-3'    (sequence No. 4)
```

(position of the bases of CK19 sequence based on Genebank accession No. 4504916 : 241-264)

(e) TaqMan probe for CK18:

```
                                    (sequence No. 5)
5'-CAAGGCATCACCAAGATTAAAGTCCTCGC-3'
```

(position of the bases of CK18 sequence based on Genebank accession No. 4557887: 1188-1160

(f) TaqMan probe for CK19:

```
5'-CGCCTGGCCTCCTACCTGGACA-3'    (sequence No. 6)
```

(position of the bases of CK19 sequence based on Genebank accession No.4504916: 268-289)

(3) RT-PCR

RT-PCR was carried out by using RT-PCR Master Reagents from Applied Biosystems.

Kit for measurement: TaqMan One-step RT-PCR Master Mix Reagents (Applied Biosystems)

cDNA synthesis: synthesized by using Multiscribe reverse transcriptase (a) Amplification of CK18

Primer for reverse transcription: primer described in sequence No. 1 was used

Primer for PCR: each primer described in sequence No. 1 and 2 was used at the final concentration of 300 nM, DNA polymerase: Ampli Taq Gold DNA polymerase was used (b) Amplification of CK19

Primer for reverse transcription: primer described in sequence No.3 was used

Primer for PCR: primers described in sequence No., 3 and 4 were used at the final concentration of 300 nM and 900 nM, respectively DNA polymerase: Ampli Taq Gold DNA polymerase was used (c) PCR Treatment Reverse transcription was done at 48° C. for 10 min, followed by holding at 95° C. for 10 min.

Then, PCR was carried out with 40 cycles of 95° C. for 15 sec and 60° C. for 1 min.

(4) Detection of Nucleic Acids

Amplification products of human CK18 and CK19 mRNA were detected fluorometrically by TaqMan probes which hybridize specifically with the target double-stranded DNA. TaqMan probes were oligonucleotides of sequence No.5 for CK18, and sequence No. 6 for CK19 whose 5' ends were labeled with FAM, 3' ends were labeled with TAMRA. Increase of the fluorescence intensity was measured in real time by PRISM7700 manufactured by Applied Biosystems.

TABLE 1

Measurement by RT-PCR
(Measured values of purified RNA samples and crude RNA samples)

| Sample | Purified RNA sample Copies/ng total RNA | Crude RNA sample Copies/ng total RNA |
|---|---|---|
| CK 18 | 2000 | 300 |
| CK 19 | 9000 | 1900 |

2) Results

The above results show the agreement of clinical results (histological diagnosis with HE staining) with the results of the measurement of RT-PCR. Amplification of mRNA was confirmed in both CK18 and CK19. Moreover, for the crude RNA sample, nucleic acid amplification was observed in both mRNA, and quantified as 300 and 1900 copies, respectively (Table. 1).

As shown above, amplification was observed in PT-PCR without extracting RNA when a buffer of pH3.0 containing Nonidet P-40 was used, thus shortening of the time required for the detection of RNA was made possible.

Example 3

Lymph node was obtained from a patient carrying breast cancer. On the samples with histologically proven metastases by HE staining, the marker for breast cancer, CK19 mRNA, was detected by RT-LAMP.

1) Materials and Methods (1) Preparation of Sample

Human lymph node was disrupted and homogenized in a buffer, with a homogenizer and a blender. The homogenate tissue was centrifuged (12000 rpm×5 min) at 4° C. and the supernatant (lysate) was collected as a crude RNA sample. To suspend tissue, a buffer containing 50 mM of potassium chloride-HCl (pH 3.0)+0.1% of Nonidet P-40, or 50mM of glycine-HCl (pH 2.2) was used. In addition, as Example 1 and 2, RNA was extracted from an aliquot of the crude RNA by using the commercially available reagent for the extraction (TRIZOL: Gibco BRL made) and was collected as purified RNA.

(2) Amplification by RT-LAMP

Amplification of CK19 was carried out by adding 2 μL of the crude RNA solution or purified RNA solution to the following composition containing 6 primers shown in sequences 7-12 below at 65° C. for 1 hour.

(3) Primers (a) 19-FA-1101:

```
5'-ttggccctcagcgtacaagagctggcctacctg-3'    (sequence No. 7)
```

(b) 19RA-1101:

```
5'-aggtcagtgtggaggtggcgcatgtcactcaggatc-3'    (sequence No. 8)
```

(c) 19-F3-1101:

```
5'-acctggagatgcagatcg-3'    (sequence No. 9)
```

(d) 19-R3-1101:

```
5'-caggcttcagcatccttc-3'    (sequence No. 10)
```

(e) 19-LPR-1101:

```
5'-tgatttcctcctcatggttc-3'    (sequence No. 11)
```

(f) 19-LPR-1101:

```
5'-tccgggcaccgatctc-3'    (sequence No. 12)
```

(4) Composition of Reaction Solution

| | |
|---|---|
| dNTPs (GIBCO made) | 0.4 mM |
| MgSO₄ | 2 mM |
| dithiothreitol | 5 mM |
| betaine (Sigma made) | 640 mM |
| Thermopol buffer (New England Biolabs made) | |
| AMV reverse transcriptase (Promega made) | 1.25 U |
| Bst DNA polymerase (New England Biolabs made) | 16 U |
| ethidium bromide | 0.125 mg/ml |
| forward inner primer (19-FA-1101: sequence No. 7) | 40 pmol |
| reverse inner primer (19-RA-1101: sequence No. 8) | 40 pmol |
| forward outer primer (19-F3-1101: sequence No. 9) | 5 pmol |
| reverse outer primer (19-R3-1101: sequence No. 10) | 5 pmol |
| forward loop primer (19-LPF-1101: sequence No. 11) | 20 pmol |
| reverse loop primer (19-LPR-1101: sequence No. 12) | 20 pmol |

(5) Detection of Nucleic Acids

Amplification products of the human CK19 mRNA were detected by fluorometry using ethidium bromide which specifically binds to double-stranded DNA. The change of fluorescent intensity of reaction solutions was measured in real time by PRISM7700 manufactured by Applied Biosystems Co., Ltd.

2) Results

Figure 2:
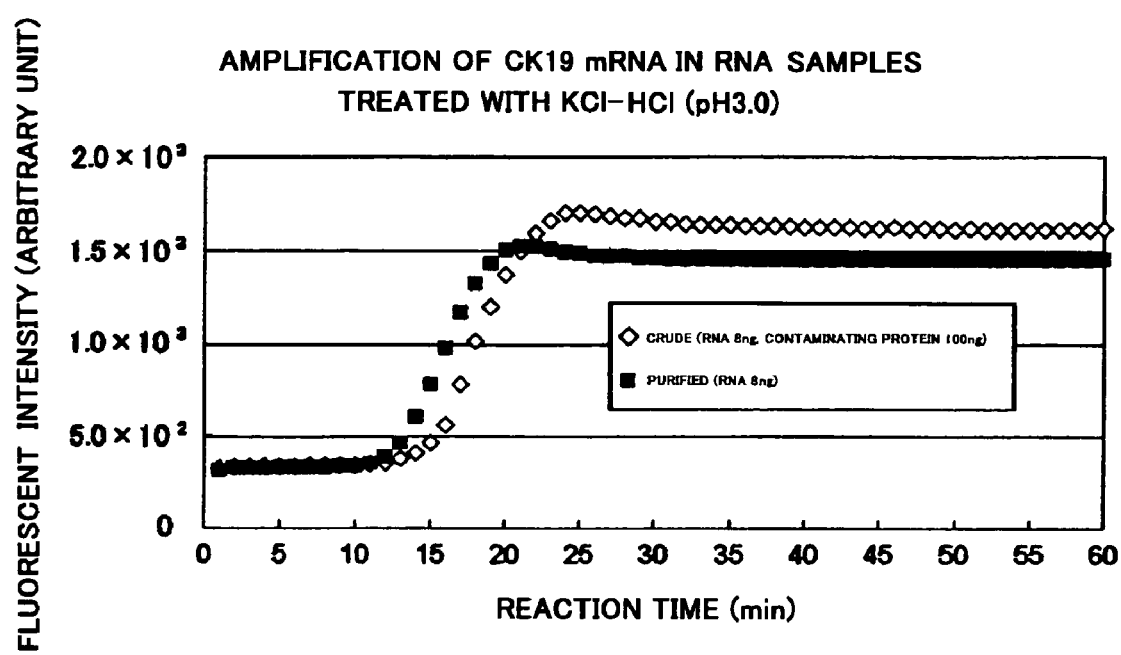
FIG. 2 shows an amplification time course of a CK19 mRNA gene product by RT-LAMP for a sample prepared by a treatment with a potassium chloride-HCl (pH 3.0)+0.1% Nonidet P-40 buffer (Example 3).
Figure 3:
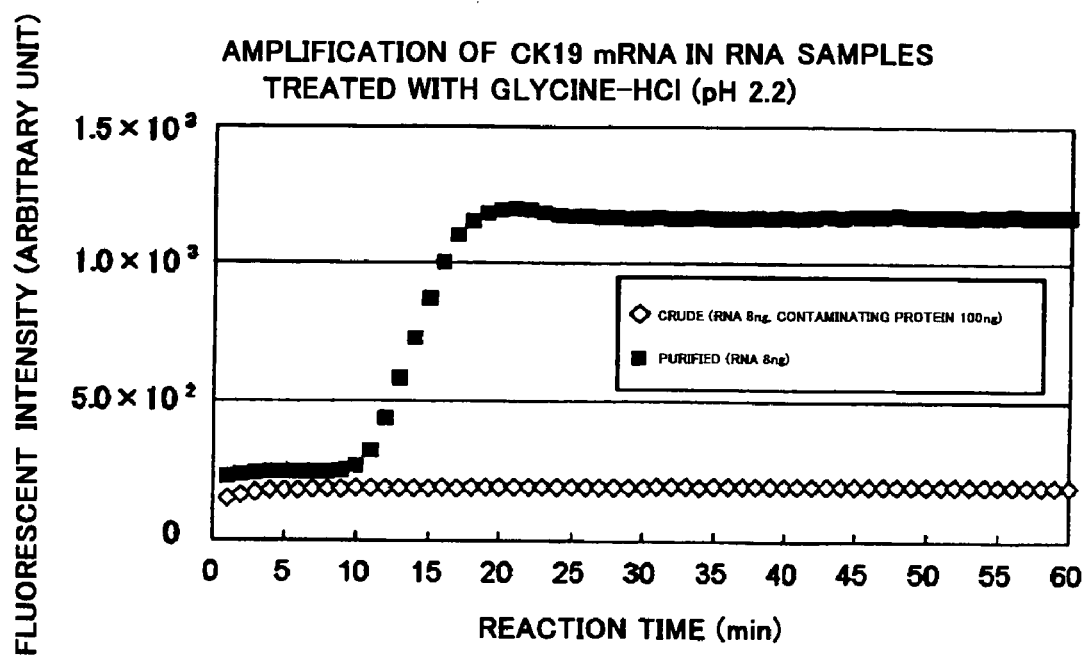
FIG. 3 shows an amplification time course of the CK19 mRNA gene product by RT-LAMP for a sample prepared by a treatment with a glycine-HCl (pH 2.2) buffer (Example 3).

Results of nucleic acid amplification by RT-LAMP in a buffer containing potassium chloride-HCl (pH 3.0)+Nonidet P-40 and a glycine-HCl (pH 2.2) buffer, which were used as buffers for preparation, were presented in FIGS. 2 and 3, respectively.

In the case of the glycine-HCl (pH 2.2) buffer, although the amplification was observed with the purified RNA sample, no amplification was observed with the crude RNA sample. In the case of the buffer containing potassium chloride-HCl (pH 3.0)+Nonidet P-40, on the other hand, amplification was observed with both purified and crude RNA samples.

As shown above, amplification is observed in RT-LAMP without extracting RNA when a buffer of pH3.0 containing Nonidet P-40 was used as preparation buffer, thus the shortening of the time required for detection of RNA became possible.

Example 4

Conditions, where inhibition of the amplification by contaminants present in amplification reaction using a crude mRNA sample was decreased, were examined by addition of a salt at the time of disruption and solubilization of a lymph node analyte.

1) Materials and Methods (1) Preparation of Samples

Mouse lymph node was disrupted and homogenized in a buffer by a blender. Cultured cells (KATOIII) were solubilized and homogenized in a buffer separately. These homogenized solutions were mixed and used as a crude RNA sample. Buffers containing 200 mM of glycine-HCl (pH 3.0)+1% of Nonidet P-40 with or without addition of 100 mM of cesium trifluoroacetate, were used in the above homogenization.

(2) Amplification by RT-LAMP

Amplification of CK19 mRNA was carried out in the following composition containing 4 primers shown in sequences 7-10 below at 65° C. for 1 hour. The above cell-solubilized sample of KATOIII cultured cells and solubilized sample of mouse lymph node were mixed at a proper ratio to give a reaction solution adjusted to contain the sample at an amount equivalent to 20 KATOIII cells and co-existing protein at a set amount as a parameter for contaminating materials.

(3) Primers (a) 19-FA-1101: (sequence No. 7)
(b) 19-RA-1101: (sequence No. 8)
(c) 19-F3-1101: (sequence No. 9)

(d) 19-R3-1101: (sequence No. 10)
(e) 19-LPF-1101: (sequence No. 11)
(f) 19-LPR-1101: (sequence No. 12)

(4) Composition of Reaction Solution

| | |
|---|---|
| dNTPs (GIBCO made) | 0.4 mM |
| MgSO$_4$ | 2 mM |
| dithiothreitol | 5 mM |
| betaine (Sigma made) | 640 mM |
| Thermopol buffer (New England Biolabs made) | |
| AMV reverse transcriptase (Promega made) | 1.25 U |
| Bst DNA polymerase (New England Biolabs made) | 16 U |
| ethidium bromide | 0.125 mg/ml |
| forward inner primer (19-FA-1101: sequence No. 7) | 40 pmol |
| reverse inner primer (19-RA-1101: sequence No. 8) | 40 pmol |
| forward outer primer (19-F3-1101: sequence No. 9) | 5 pmol |
| reverse outer primer (19-R3-1101: sequence No. 10) | 5 pmol |
| forward loop primer (19-LPF-1101: sequence No. 11) | 20 pmol |
| reverse loop primer (19-LPR-1101: sequence No. 12) | 20 pmol |

(5) Detection of Nucleic Acids

Detection was carried out by measuring fluorescence of ethidium bromide contained in the reaction. The change of fluorescent intensity in the reaction solution was measured in real time by PRISM7000 manufactured by Applied Biosystems Co., Ltd.

2) Results

Figure 4:
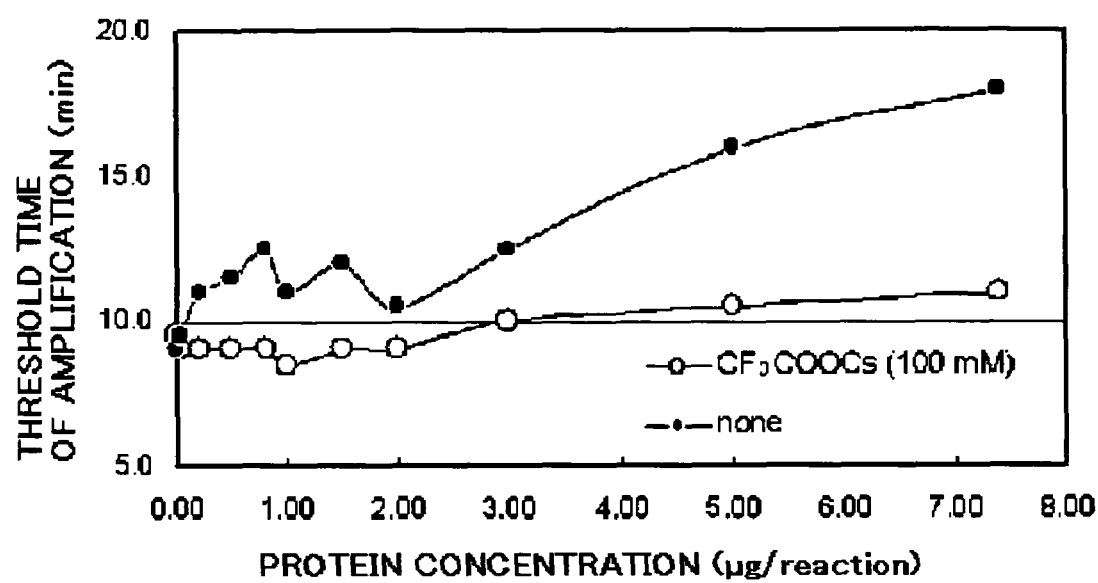
FIG. 4 shows a comparison of a threshold time of an amplification of the CK19 mRNA gene product with or without an addition of cesium trifluoroacetate (Example 4).

The results obtained in a buffer containing 200 mM of glycine-HCl (pH 3.0)+100 mM of cesium trifluoroacetate+1% of Nonidet P-40 or a buffer containing 200 mM of glycine-HCl (pH 3.0)+1% of Nonidet P-40 without cesium trifluoroacetate, which were used as buffers for preparation of crude RNA samples, are presented in FIG. 4. The axis of abscissas depicts the amount of contaminating protein in the assay, and the axis of ordinates depicts the threshold time of DNA amplification. The threshold time of amplification showed little change even in the presence of nearly 8 μg of contaminating protein in the assay, when cesium trifluoroacetate was included in the buffer for the preparation of RNA samples. On the contrary, when cesium trifluoroacetate was absent, threshold time of DNA amplification was clearly delayed along with the increase of the amount of contaminating protein. That is to say, it is indicated that nucleic acid amplification is inhibited by contaminating protein. Addition of 100 mM of cesium trifluoroacetate to the buffer used for preparing crude RNA sample can reduce inhibition of the amplification reaction by the contaminating protein. As the result, it enables the improvement of sensitivity by the increase of amount of additive crude RNA sample in the assay.

Example 5

An attempt was made to improve detection sensitivity by preventing degradation of the target mRNA with RNase through addition of an RNase inhibitor upon amplification reaction using crude RNA samples from lymph node analyte.

1) Materials and Methods (1) Preparation of Samples

Lymph node from a patient carrying breast cancer was disrupted and homogenized with the blender in buffers containing 200 mM of glycine-HCl (pH 3.0)+1% of Nonidet P-40 with or without addition of 100 mM of cesium trifluoroacetate. The homogenized solution was used as a crude RNA sample without dilution, or after a 5- or a 50-fold dilution with the buffer used for homogenization.

(2) Amplification by RT-LAMP

Amplification of β-actin was carried out by adding 2 μL of the above crude RNA sample to the following composition containing 6 primers shown in sequence Nos. 13-18 below at 65° C. for 1 hour.

(3) Primers (a) AFA-4:

(sequence No. 13)
(a) AFA-4:
5'-tgaaggtagtttcgtggatgcctgaggcactcttccagc-3'

(sequence No. 14)
(b) ARA-4:
5'-tgaagtgtgacgtggacatccagggtacatggtggtgc-3'

(sequence No. 15)
(c) AF3-4:
5'-tggcaatgagcggttcc-3'

(sequence No. 16)
(d) AR3-4:
5'-tccttctgcatcctgtcg-3'

(sequence No. 17)
(e) AD-LPF1:
5'-acaggactccatgccc-3'

(sequence No. 18)
(f) AD-LPR1:
5'-tgtacgccaacacagtgc-3'

(4) Composition of Reaction Solution

| | |
|---|---|
| dNTPs (GIBCO made) | 0.4 mM |
| MgSO$_4$ | 2 mM |
| dithiothreitol | 5 mM |
| betaine (Sigma made) | 640 mM |
| Thermopol buffer (New England Biolabs made) | |
| AMV reverse transcriptase (Promega made) | 1.25 U |
| Bst DNA polymerase (New England Biolabs made) | 16 U |
| ethidium bromide | 0.125 mg/ml |
| forward inner primer (AFA-4: sequence No. 13) | 40 pmol |
| reverse inner primer (ARA-4: sequence No. 14) | 40 pmol |
| forward outer primer (AF3-4: sequence No. 15) | 5 pmol |
| reverse outer primer (AR3-4: sequence No. 16) | 5 pmol |
| forward loop primer (AD-LPF1: sequence No. 17) | 20 pmol |
| reverse loop primer (AD-LPR1: sequence No. 18) | 20 pmol |
| RNase inhibitor | 25 U |
| (Stratagene made, RNase Block Ribonuclease Inhibitor) | |

(5) Detection of Nucleic Acids

Amplification products were detected by measuring fluorescence of ethidium bromide contained in the reaction. Change of fluorescent intensity of the reaction solution was measured in real time by PRISM7700 manufactured by Applied Biosystems Co., Ltd.

2) Results

Figure 5:
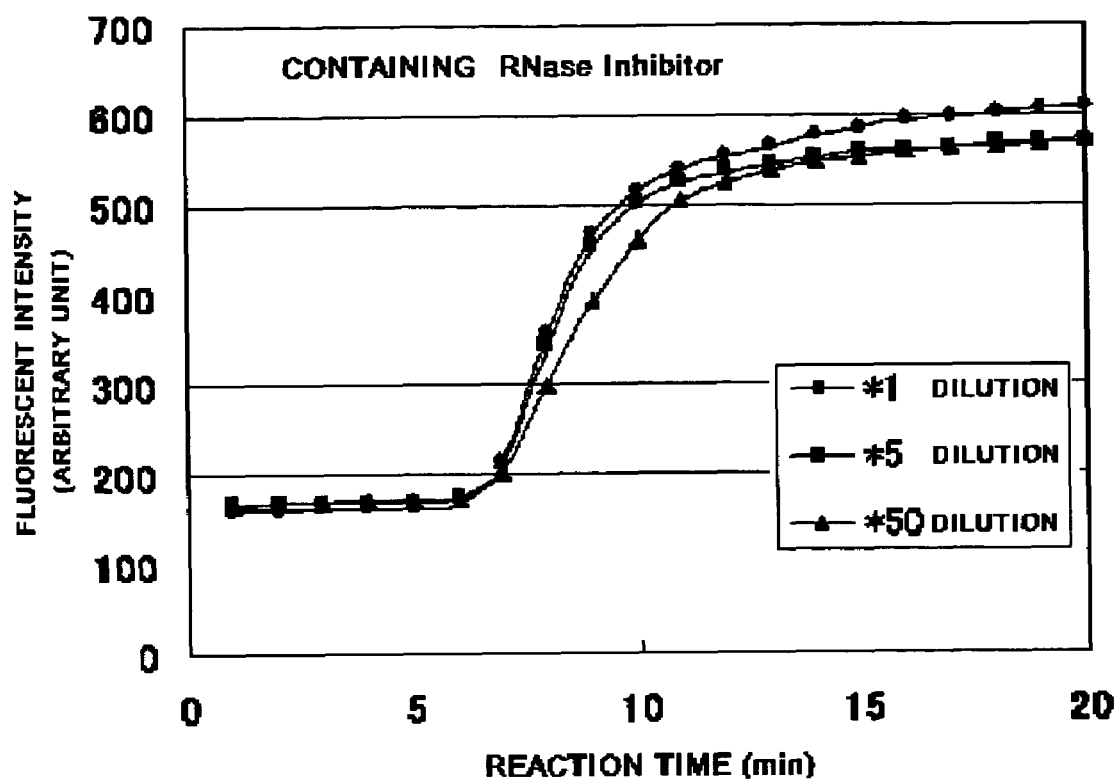
FIGS. 5 and 6 show a comparison of an amplification of a β-actin mRNA gene product with or without an addition of an RNase inhibitor (Example 5).
Figure 6:
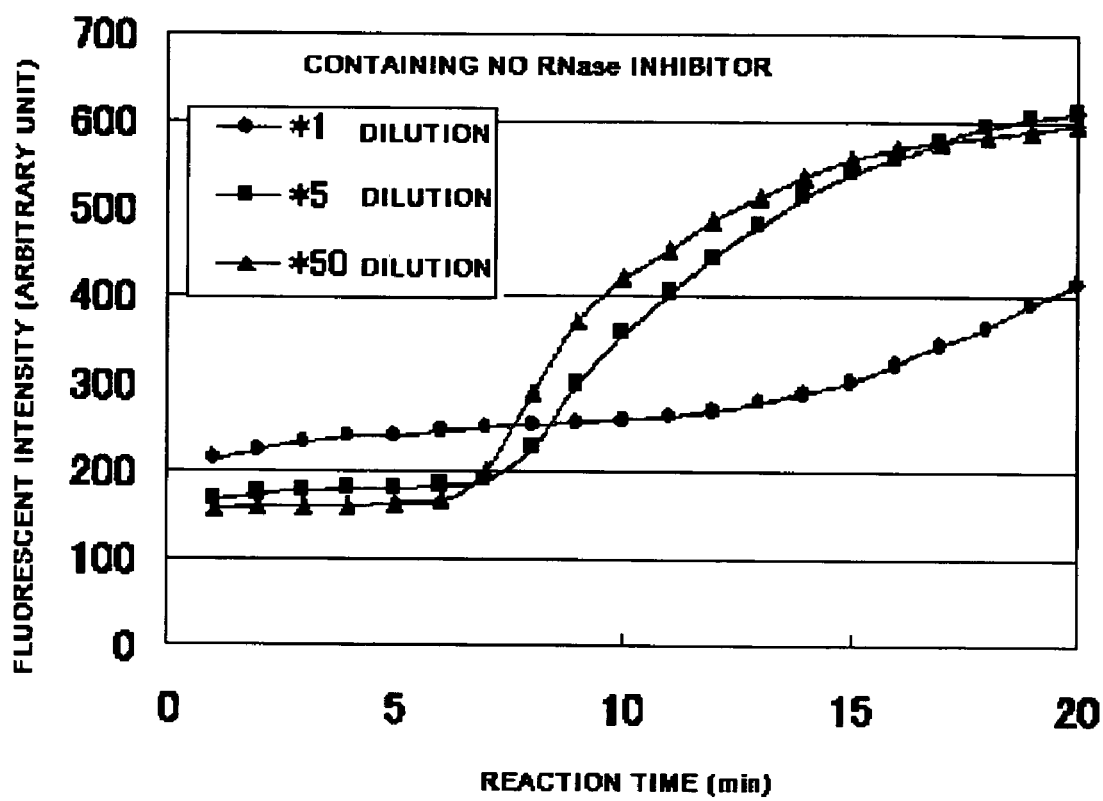

Results in the presence or absence of RNase inhibitor in the solution for amplification reaction are shown in FIGS. 5 and 6, respectively. The axis of abscissas depicts reaction time and the axis of ordinates depicts fluorescent intensity. In the case where the RNase inhibitor was contained in the reaction solution, no inhibition occurred for the crude RNA sample by homogenizing human lymph node and its 5- or 50-fold diluted samples. On the contrary, inhibition of amplification reaction took place and almost no amplification was observed particularly in the crude RNA sample without dilution when RNase inhibitor was absent in the reaction solution. Based on these facts, it becomes possible to decrease inhibition of contaminating protein on amplification reaction by addition of RNase inhibitor at a concentration of 25 U to the buffer used for crude RNA. As the result, it enables the improvement of sensitivity by the increase of additive crude RNA sample in the assay.

Example 6

Under a condition where 100 mM of cesium trifluoroacetate was added to a buffer for disrupting and homogenizing lymph node and 25 U of RNase inhibitor was added to a solution for amplification reaction, lymph node from a patient carrying breast cancer was actually used to confirm effect of these additives.

1) Materials and Methods (1) Preparation of Samples

Lymph node from a patient carrying breast cancer was disrupted and homogenized with the blender in buffers containing 200 mM of glycine-HCl (pH 3.0)+1% of Nonidet P-40 with or without addition of 10 mM of cesium trifluoroacetate, respectively. Homogenized solutions were diluted 5 fold with the buffer used for homogenization and were used as a crude RNA sample for amplification reaction by RT-LAMP. In order to estimate numbers of copy of CK19 mRNA, RNA was extracted and purified from the crude RNA by the commercially available reagent for extraction (TRIZOL: Gibco BRL made) as described in Example 1, which was used as a purified RNA sample in RT-PCR. RT-PCR was carried under similar conditions as in Example 1.

(2) Amplification by RT-LAMP

Amplification of CK19 mRNA was carried out in the following composition containing 6 primers shown in sequences 7-12 below at 65° C. for 1 hour. When the crude RNA sample homogenized in the presence of cesium trifluoroacetate, amplification reaction was performed using a reaction solution with an RNase inhibitor.

(3) Primers
(a) 19-FA-1101: (sequence No. 7)
(b) 19-RA-1101: (sequence No. 8)
(c) 19-F3-1101: (sequence No. 9)
(d) 19-R3-1101: (sequence No. 10)
(e) 19-LPF-1101: (sequence No. 11)
(f) 19-LPR-1101: (sequence No. 12)

(4) Composition of Reaction Solution

| | |
|---|---|
| dNTPs (GIBCO made) | 0.4 mM |
| MgSO$_4$ | 2 mM |
| dithiothreitol | 5 mM |
| betaine (Sigma made) | 640 mM |
| Thermopol buffer (New England Biolabs made) | |
| AMV reverse transcriptase (Promega made) | 1.25 U |
| Bst DNA polymerase (New England Biolabs made) | 16 U |
| ethidium bromide | 0.125 mg/ml |
| forward inner primer (19-FA-1101: sequence No. 7) | 40 pmol |
| reverse inner primer (19-RA-1101: sequence No. 8) | 40 pmol |
| forward outer primer (19-F3-1101: sequence No. 9) | 5 pmol |
| reverse outer primer (19-R3-1101: sequence No. 10) | 5 pmol |
| forward loop primer (19-LPF-1101: sequence No. 11) | 20 pmol |
| reverse loop primer (19-LPR-1101: sequence No. 12) | 20 pmol |
| RNase inhibitor (Stratagene made, RNase Block Ribonuclease Inhibitor) | 25 U |

(5) Detection of Nucleic Acids

Detection of amplification products was carried out with fluorescence of ethidium bromide contained in the reaction. The change of fluorescent intensity of the reaction solution was measured in real time by PRISM7700 manufactured by Applied Biosystems Co., Ltd.

(2) Results

Results obtained in the presence or absence of cesiumcesium trifluoroacetate and the RNase inhibitor in the solution of amplification reaction are shown in Table 2. The left of the table shows the result without cesium trifluoroacetate and the RNase inhibitor. The right half shows the result with both cesium trifluoroacetate and the RNase inhibitor. In the absence of both additives, CK19 mRNA was not detected by RT-LAMP in 4 samples tested, whereas in the presence of the both, CK19 mRNA could be amplified and detected in 3 samples out of 4. Thus it was confirmed for human lymph node that co-existence of trifluoroacetic acid upon disruption and solubilization of it and addition of an RNase inhibitor to a reaction solution is effective to improve detection sensitivity.

TABLE 2

Measurement of the amount of CK19 mRNA by RT-PCR and RT-LAMP

| SAMPlE No. | PROTEIN (mg/μL) | CK19 mRNA (copy number/μL) | | SAMPlE No. | PROTEIN (mg/μL) | CK19 mRNA (copy number/μL) | |
|---|---|---|---|---|---|---|---|
| | | PCR | LAMP | | | PCR | LAMP |
| 33 (HE+) | 0.76 | 70 | ND | 102 (HE+) | 0.44 | 60 | ND |
| 41 (HE+) | 3.0 | 380 | ND | 118 (HE+) | 8.2 | <400 | 300 |
| 94 (HE+) | 6.8 | 1,880 | ND | 149 (HE+) | 7.9 | 90 | 650 |
| 126 (HE-/IHC+) | 3.8 | 620 | ND | 150 (HE-) | 5.5 | 70 | <500 |

Example 7

Effect of cesium trifluoroacetate was confirmed by RT-PCR using serum directly.

1) Materials and Methods (1) Preparation of Sample

To humane serum, a buffer (pH 8.0) containing 200 mM of Tris-HCl or a buffer (pH 3.0) containing 200 mM of glycine-HCl +100 mM of cesium trifluoroacetate was added, to each of which a purified RNA sample from KATOIII cells was further added to be used as an RNA sample. Protein concentration in the sample was adjusted to be 0 to 33 µg/µL. Also, the amount of CK19 mRNA was adjusted to be 5000 copies/µL in the assay.

(2) Sequence of primers and probes used (a) CK19 Reverse Primer:

```
5'-cttggccctcagcgtact-3'    (sequence No. 19)
```

(Base position of CK19 sequence based on Genbank accession No. 4504916 685-667)

(b) CK19 Forward Primer:

```
5'-cagatcgaaggcctgaagga-3'    (sequence No. 20)
```

(Base position of CK19 sequence based on Genbank accession No. 4504916 607-626)

(c) TaqMan Probe for CK19:

```
                              (sequence No. 21)
5'-gcctacctgaagaagaaccatgaggaggaa-3'
```

21)

(Base position of CK19 sequence based on Genbank accession No. 4504916 634-663)

(3) RT-PCR

RT-PCR was carried out by RT-PCR master reagents from Applied Biosystems.

Assay kit: TaqMan One-step RT-PCR Master Mix Reagents (Applied Biosystems made)

cDNA synthesis: synthesized by using MultiScribe reverse transcriptase

① Amplification of CK19

Primer for reverse transcription: primer described in sequence No. 19 was used

Primer for PCR: primer described in sequence No. 19 and primer described in sequence No. 20 were used at the final concentrations of 300 nM and 900 nM, respectively DNA polymerase: Ampli Taq Gold DNA polymerase was used

③ PCR

Reverse transcriptase reaction was conducted at 48° C. for 30 min and incubated 95° C. for 10 min.

Then, PCR operation was carried out with 40 cycles of 95° C. for 15 sec and 60° C. for 1 min.

(4) Detection of Nucleic Acids

Amplification products of human CK19 mRNA were detected fluorometrically with TaqMan probes which hybridize specifically to the target double-stranded DNA. TaqMan probes for CK19 were oligonucleotides of sequence No. 21 whose 5' end and 3' end were labeled with FAM and TAMRA, respectively. Increase of fluorescence intensity in the reaction solution was measured in real time by PRISM7700 manufactured by Applied Biosystems.

2) Results

Figure 7:
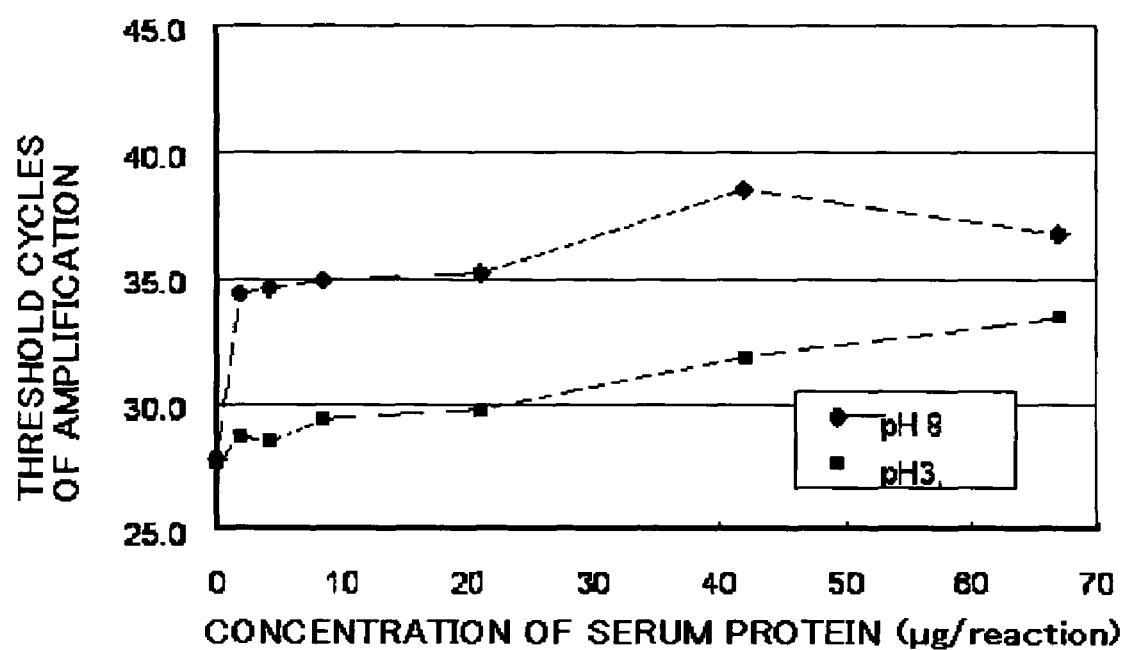
FIG. 7 shows a comparison of threshold cycles for starting up of the amplification of CK19 mRNA gene products in buffers having different pH (Example 7).

FIG. 7 shows the results of RT-PCR on RNA samples containing serum components prepared in a buffer (pH 3) containing cesium trifluoroacetate and in a neutral buffer (pH 8), respectively. Square plot in the figure represents the result with the buffer (pH 3) containing cesium trifluoroacetate, and diamond plot represents the result with the neutral buffer. The axis of ordinates depicts the threshold of cycles of amplification in RT-PCR reaction. The axis of abscissas depicts amount of serum proteins present in the reaction. The RNA sample prepared in the neutral buffer suffered inhibition of amplification reaction resulting in increase in the threshold cycles of amplification when the serum protein was contained. On the other hand, the RNA sample prepared in the acidic buffer containing cesium trifluoroacetate was inhibited to a small extent resulting in little increase in the number of cycles. Thus, it was confirmed that preparation of the RNA sample using an acidic buffer (pH 3) containing cesium trifluoroacetate is effective not only in prevention of the inhibition of amplification reaction in RT-LAMP, but also in RT-PCR reaction.

INDUSTRIAL APPLICABILITY

As explained above, in methods for detecting RNA by nucleic acid amplification, it was confirmed that, the condition for preparing a testing sample according to the present invention allows even a crude RNA sample to be measured by RT-PCR and RT-LAMP. Thus, shortening of assay time using means for nucleic acid amplification can be achieved.

---

The invention claimed is:

1. A method for direct nucleic acid amplification, comprising:
   (A) admixing a buffer solution having an acidic pH, a surfactant and a biological sample which comprises a nucleic acid component, wherein the acidic pH is in the range of pH 2.5 to pH 5,
   (B) homogenizing the resulting mixture of step (A),
   (C) preparing a reaction solution comprising the resulting homogenized mixture of step (B), a primer and a DNA polymerase, without separating the nucleic acid component from a liquid phase of the resulting homogenized mixture of step (B), and
   (D) amplifying a target nucleotide sequence within the nucleic acid component in the resulting reaction solution of step (C).

2. The method according to claim 1, wherein the reaction solution of step (C) further comprises a nuclease inhibitor.

3. The method according to claim 1, wherein step (A) further comprises admixing a salt, which interacts with an inhibitor of said nucleic acid amplification reaction, with said buffer solution and said biological sample.

4. The method according to claim 2, wherein the nuclease inhibitor is an RNase inhibitor.

5. The method according to claim 3, wherein the salt is a chaotropic salt.

6. The method according to claim 3, wherein the salt is an alkaline metal salt of trihaloacetic acid.

7. The method according to claim 1, wherein the biological sample is lymph node.

8. The method according to claim 1, wherein the target nucleotide sequence is selected from the group consisting of a cancer marker and a tumor associated marker.

9. The method according to claim 8, wherein the tumor associated marker is selected from the group consisting of cytokeratin 18, cytokeratin 19, cytokeratin 20 and CEA.

10. The method according to claim 1, wherein step (D) is carried out by a method selected from the group consisting of LAMP, RT-LAMP, PCR and RT-PCR.

11. The method according to claim 1, which further comprises:
    (E) detecting the resulting amplification product of step (D).

12. The method according to claim 3, wherein the salt is at least one member selected from the group consisting of NaCl, KCl, NaI, KI, TMACl (tetramethyl ammonium chloride), TEACl (tetraethyl ammonium chloride), KSCN, CsSCN and CsCl.

13. The method according to claim 3, wherein said salt is $CF_3COOCs$ (cesium trifluoroacetate).

14. The method according to claim 3, wherein the biological sample is further treated with an anionic solid material before amplifying said target nucleotide sequence.

15. The method according to claim 1, wherein the biological sample is tissue collected from a living body.

* * * * *

SEQUENCE LISTING

```
<160> NUMBER OF SEQ ID NOS: 21

<210> SEQ ID NO 1
<211> LENGTH: 21
<212> TYPE: DNA
<213> ORGANISM: Artificial Sequence
<220> FEATURE:
<223> OTHER INFORMATION: Designed DNA based on CK18 gene

<400> SEQUENCE: 1
```

-continued

```
gatggtttgc atggagttgc t                                          21
```

<210> SEQ ID NO 2
<211> LENGTH: 17
<212> TYPE: DNA
<213> ORGANISM: Artificial Sequence
<220> FEATURE:
<223> OTHER INFORMATION: Designed DNA based on CK18 gene

<400> SEQUENCE: 2

```
gccgcctgct ggaagat                                               17
```

<210> SEQ ID NO 3
<211> LENGTH: 14
<212> TYPE: DNA
<213> ORGANISM: Artificial Sequence
<220> FEATURE:
<223> OTHER INFORMATION: Designed DNA based on CK19 gene

<400> SEQUENCE: 3

```
tccagggcgc gcac                                                  14
```

<210> SEQ ID NO 4
<211> LENGTH: 24
<212> TYPE: DNA
<213> ORGANISM: Artificial Sequence
<220> FEATURE:
<223> OTHER INFORMATION: Designed DNA based on CK19 gene

<400> SEQUENCE: 4

```
aagctaacca tgcagaacct caac                                       24
```

<210> SEQ ID NO 5
<211> LENGTH: 29
<212> TYPE: DNA
<213> ORGANISM: Artificial Sequence
<220> FEATURE:
<223> OTHER INFORMATION: Designed DNA based on CK18 gene

<400> SEQUENCE: 5

```
caaggcatca ccaagattaa agtcctcgc                                  29
```

<210> SEQ ID NO 6
<211> LENGTH: 22
<212> TYPE: DNA
<213> ORGANISM: Artificial Sequence
<220> FEATURE:
<223> OTHER INFORMATION: Designed DNA based on CK19 gene

<400> SEQUENCE: 6

```
cgcctggcct cctacctgga ca                                         22
```

<210> SEQ ID NO 7
<211> LENGTH: 34
<212> TYPE: DNA
<213> ORGANISM: Artificial Sequence
<220> FEATURE:
<223> OTHER INFORMATION: Designed DNA based on CK19 gene

<400> SEQUENCE: 7

```
ttggcccctc agcgtacaag agctggccta cctg                            34
```

<210> SEQ ID NO 8
<211> LENGTH: 36
<212> TYPE: DNA
<213> ORGANISM: Artificial Sequence

```
<220> FEATURE:
<223> OTHER INFORMATION: Designed DNA based on CK19 gene

<400> SEQUENCE: 8
aggtcagtgt ggaggtggcg catgtcactc aggatc                              36

<210> SEQ ID NO 9
<211> LENGTH: 18
<212> TYPE: DNA
<213> ORGANISM: Artificial Sequence
<220> FEATURE:
<223> OTHER INFORMATION: Designed DNA based on CK19 gene

<400> SEQUENCE: 9
acctggagat gcagatcg                                                  18

<210> SEQ ID NO 10
<211> LENGTH: 18
<212> TYPE: DNA
<213> ORGANISM: Artificial Sequence
<220> FEATURE:
<223> OTHER INFORMATION: Designed DNA based on CK19 gene

<400> SEQUENCE: 10
caggcttcag catccttc                                                  18

<210> SEQ ID NO 11
<211> LENGTH: 20
<212> TYPE: DNA
<213> ORGANISM: Artificial Sequence
<220> FEATURE:
<223> OTHER INFORMATION: Designed DNA based on CK19 gene

<400> SEQUENCE: 11
tgatttcctc ctcatggttc                                                20

<210> SEQ ID NO 12
<211> LENGTH: 16
<212> TYPE: DNA
<213> ORGANISM: Artificial Sequence
<220> FEATURE:
<223> OTHER INFORMATION: Designed DNA based on CK19 gene

<400> SEQUENCE: 12
tccgggcacc gatctc                                                    16

<210> SEQ ID NO 13
<211> LENGTH: 39
<212> TYPE: DNA
<213> ORGANISM: Artificial Sequence
<220> FEATURE:
<223> OTHER INFORMATION: Designed DNA based on Beta-actin gene

<400> SEQUENCE: 13
tgaaggtagt ttcgtggatg cctgaggcac tcttccagc                           39

<210> SEQ ID NO 14
<211> LENGTH: 38
<212> TYPE: DNA
<213> ORGANISM: Artificial Sequence
<220> FEATURE:
<223> OTHER INFORMATION: Designed DNA based on Beta-actin gene

<400> SEQUENCE: 14
tgaagtgtga cgtggacatc cagggtacat ggtggtgc                            38
```

<210> SEQ ID NO 15
<211> LENGTH: 17
<212> TYPE: DNA
<213> ORGANISM: Artificial Sequence
<220> FEATURE:
<223> OTHER INFORMATION: Designed DNA based on Beta-actin gene

<400> SEQUENCE: 15
tggcaatgag cggttcc                                              17

<210> SEQ ID NO 16
<211> LENGTH: 18
<212> TYPE: DNA
<213> ORGANISM: Artificial Sequence
<220> FEATURE:
<223> OTHER INFORMATION: Designed DNA based on Beta-actin gene

<400> SEQUENCE: 16
tccttctgca tcctgtcg                                             18

<210> SEQ ID NO 17
<211> LENGTH: 16
<212> TYPE: DNA
<213> ORGANISM: Artificial Sequence
<220> FEATURE:
<223> OTHER INFORMATION: Designed DNA based on Beta-actin gene

<400> SEQUENCE: 17
acaggactcc atgccc                                               16

<210> SEQ ID NO 18
<211> LENGTH: 18
<212> TYPE: DNA
<213> ORGANISM: Artificial Sequence
<220> FEATURE:
<223> OTHER INFORMATION: Designed DNA based on Beta-actin gene

<400> SEQUENCE: 18
tgtacgccaa cacagtgc                                             18

<210> SEQ ID NO 19
<211> LENGTH: 19
<212> TYPE: DNA
<213> ORGANISM: Artificial Sequence
<220> FEATURE:
<223> OTHER INFORMATION: Designed DNA based on CK19 gene

<400> SEQUENCE: 19
cttggcccct cagcgtact                                            19

<210> SEQ ID NO 20
<211> LENGTH: 20
<212> TYPE: DNA
<213> ORGANISM: Artificial Sequence
<220> FEATURE:
<223> OTHER INFORMATION: Designed DNA based on CK19 gene

<400> SEQUENCE: 20
cagatcgaag gcctgaagga                                           20

<210> SEQ ID NO 21
<211> LENGTH: 30
<212> TYPE: DNA
<213> ORGANISM: Artificial Sequence
<220> FEATURE:
<223> OTHER INFORMATION: Designed DNA based on CK19 gene -continued

```
<400> SEQUENCE: 21
gcctacctga agaagaacca tgaggaggaa                              30
```